United States Patent

Evans et al.

[11] Patent Number: 5,386,715
[45] Date of Patent: Feb. 7, 1995

[54] GAS VAPOR SENSOR

[75] Inventors: Keenan L. Evans; Young S. Chung, both of Tempe; William Glaunsinger, Chandler; Ian W. Sorensen, Phoenix, all of Ariz.

[73] Assignee: Motorola, Inc., Schaumburg, Ill.

[21] Appl. No.: 161,624

[22] Filed: Dec. 6, 1993

[51] Int. Cl.$^6$ ...................... H01L 29/60; G01N 27/00
[52] U.S. Cl. ................... 73/31.05; 257/414; 204/431; 324/71.5
[58] Field of Search ....................... 73/31.05; 324/71.5, 324/71.1; 257/453, 414; 204/426, 431

[56] References Cited

U.S. PATENT DOCUMENTS

| | | | |
|---|---|---|---|
| 4,782,302 | 11/1988 | Bastasz et al. | 324/71.3 |
| 4,836,012 | 6/1989 | Doty et al. | 324/71.5 X |
| 4,878,015 | 10/1989 | Schmidt et al. | 324/71.5 |
| 4,931,851 | 6/1990 | Sibbald et al. | 357/25 |
| 4,973,910 | 11/1990 | Wilson | 324/457 |
| 5,302,274 | 4/1994 | Tomantschger et al. | 204/426 X |

FOREIGN PATENT DOCUMENTS

| | | | |
|---|---|---|---|
| 0488352 | 6/1992 | European Pat. Off. | 73/31.06 |
| 3-277953 | 12/1991 | Japan | 73/31.06 |
| 4-323548 | 11/1992 | Japan | 73/31.05 |
| 5-164719 | 6/1993 | Japan | 73/31.05 |

OTHER PUBLICATIONS

K. Evans et al., "Effect of Phospine on the Work Function Change", Materials Developments in Microelectronic Packaging Conference Proceedings, pp. 359–364, Aug. 19–22, 1991.

X. L. Zhou et al., "A Comparative Study of PF$_3$, PH$_3$ and P(CH$_3$)$_3$ On Clean, K–Covered Ag(111)", Surface Science 221, 1989, pp. 534–552.

*Primary Examiner*—Hezron E. Williams
*Assistant Examiner*—J. David Wiggins
*Attorney, Agent, or Firm*—William E. Koch

[57] ABSTRACT

An embodiment of a sensing element (10) for a gas vapor detector (24) is formed from a gold-palladium alloy. The sensing element (10) is highly sensitive to phosphine or arsine gas. The by volume palladium concentration of the sensing element is typically less than 20%. The sensing element (10) is used as an active element in a gas vapor detector (24).

9 Claims, 1 Drawing Sheet

GAS VAPOR SENSOR

BACKGROUND OF THE INVENTION

The present invention relates, in general, to apparatus for detecting gas vapors, and more particularly, to a novel sensor element for a gas vapor detector.

In the past, a variety of materials have been utilized as sensing elements within gas vapor detectors. The material utilized to form the sensor element typically is determined by the gas to be detected. For example, some typical materials utilized for detecting phosphine gas include rhodium, potassium covered silver, oxidized iron, or gold. One disadvantage of these prior sensing elements is the gas concentration that can be detected. These prior sensors generally cannot detect phosphine concentrations that are less than about 10 parts per billion. Additionally, the prior sensors cannot detect such low levels of arsine gas.

Both phosphine and arsine are commonly used materials in semiconductor processing areas. Since both gases are highly toxic, it is desirable to detect even the smallest amount of either gas in the environment.

Accordingly, it is desirable to have a gas vapor sensor element that facilitates detecting phosphine concentrations of less than approximately one part per billion, and that facilitates detecting arsine concentrations of less than approximately one part per billion.

DETAILED DESCRIPTION OF THE DRAWINGS

Figure 1:
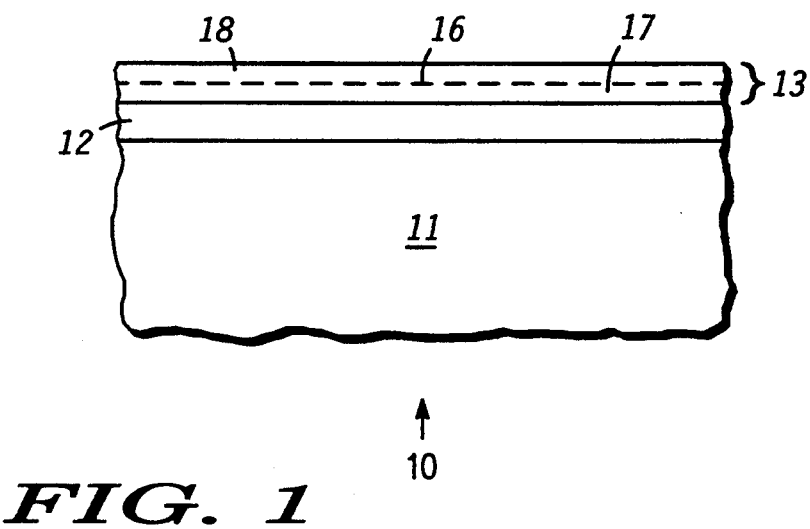
FIG. 1 illustrates an enlarged cross-sectional portion of an embodiment of a gas vapor sensor element in accordance with the present invention.

FIG. 1 illustrates an enlarged portion of an embodiment of a gas vapor sensor element 10 that is suitable for use in a gas vapor detecting apparatus or gas detector. Element 10 includes a supporting substrate 11, an intermediate layer 12 on a surface of substrate 11, and an active layer 13 on layer 12. Substrate 11 is utilized to support active layer 13 and preferably is silicon, but can also be a variety of other materials including silicon dioxide, silicon nitride, aluminum nitride, aluminum oxide, quartz, glass, and mica. Layer 12 provides a continuous surface and functions as an adhesive that ensures layer 13 adheres to substrate 11. Preferably, layer 12 is approximately thirty to fifty nanometers of silicon dioxide that is applied to substrate 11 by techniques that are well known to those skilled in the semiconductor art. Other materials that provide a continuous surface and do not react with layer 13, such as silicon nitride, may also be employed for layer 12. Layer 12 may be omitted if the surface of substrate 11 is suitable for forming a continuous layer 13. In order to facilitate sensing low levels of phosphine or arsine gas, active layer 13 includes a gold-palladium alloy having a by volume palladium concentration of approximately one percent to twenty percent. Higher palladium concentrations may result in a layer of palladium oxide on the surface of layer 13 thereby reducing the efficiency of layer 13. An electrical terminal (not shown) allows connecting layer 13 to electrical circuitry (not shown) that facilitates determining the concentration of gas sensed by element 10.

Layer 13 is formed by applying two separate materials, then annealing them into one homogeneous layer. For purpose of explanation the two layers are illustrated by dividing layer 13 with a dashed line 16. A layer of palladium 17 is deposited onto the surface of layer 12 by low pressure evaporation or other means that are well known to those skilled in the semiconductor art. Subsequently, a layer of gold 18 is deposited onto palladium 17 by techniques that are well known to those skilled in the semiconductor art. In the preferred embodiment, palladium 17 and gold 18 have a thickness of approximately six nanometers and fifty-four nanometers, respectively. Also in the preferred embodiment, layer 13 is approximately one centimeter square. One example of such deposition techniques is described in an article by K. Evans et al. "Effect Of Phosphine On The Work Function Change", Microelectronic Packaging Conference Proceedings, August 19-22, 1991, pp. 359-364. In order to prevent oxidation of palladium 17, it is important to deposit the palladium first then cover with the gold. If palladium 17 is not exposed to oxygen, the deposition sequence is not important since the palladium oxidation is no longer a concern. After deposition, layer 13 is formed by annealing palladium 17 and gold 18 in an inert gas such as nitrogen or argon in order to form a homogeneous gold-palladium alloy film. The annealing is accomplished at a temperature of 300 to 500 degrees Celsius (°C.) for a time between one hour and five minutes, respectively. The resulting thickness of layer 13 is approximately fifty to seventy nanometers.

In an alternate embodiment, active layer 13 is a layer of gold having a thickness of approximately fifty to seventy nanometers. The gold layer is formed by low pressure evaporation or other deposition means that are well known to those skilled in the semiconductor art. Thereafter, the gold layer is annealed, similarly to the gold-palladium layer, to form a homogeneous gold film.

Figure 2:
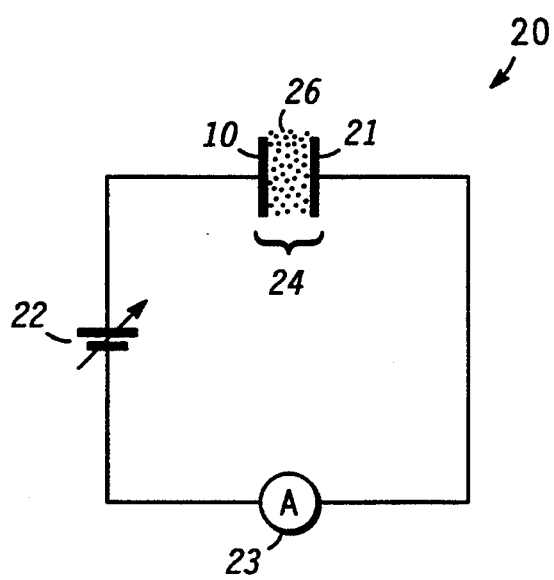
FIG. 2 schematically illustrates an electrical circuit for utilizing the gas vapor sensor element of FIG. 1.

FIG. 2 schematically illustrates a gas vapor sensing circuit 20 that includes a gas detector 24, a variable voltage source 22, and an ammeter 23 that are electrically connected in series. Detector 24 functions electrically as a capacitor having a first plate that is element 10 of FIG. 1, and a reference element 21 functioning as the second capacitor plate. Reference element 21 is a material that is inert in the gas vapor that is to be detected, and typically is either stainless steel or chromiated gold. Since elements 10 and 21 are different materials, the work function voltage of each material is different. This difference in work function voltage results in a differential voltage between elements 10 and 21. As will be seen hereinafter, this differential voltage facilitates detecting a gas that passes between elements 10 and 21.

By periodically varying the distance between the plates of the capacitor, a current is induced to flow through ammeter 23. The current is proportional to the difference between the voltage applied by source 22 and differential voltage created by the different work function voltages of elements 10 and 21. By adjusting voltage source 22 to a value that is equal to the differential voltage, that is, the difference between the work function voltages, the current becomes zero (null condition). Such an apparatus is generally referred to as a Kelvin probe and is well known to those skilled in the art. In order to detect a gas, detector 24 is calibrated by exposing elements 10 and 21 to air, and adjusting voltage source 22 until there is no current flow through ammeter 23. Upon exposing element 10 to a gas vapor 26, for example an arsine or phosphine containing gas vapor, the gas within vapor 26 modifies the work function voltage of element 10. As the work function voltage changes, the differential voltage also changes thereby causing current to flow through ammeter 23. The value of this current is determined by the concentration of the gas in vapor 26. Consequently, the gas concentration can be determined by measuring either the current or the modified differential voltage. Therefore, the presence and concentration of the gas in vapor 26 can be determined by detecting the change in the work function voltage of element 10. In the preferred embodiment, the differential voltage is monitored to detect the gas in vapor 26. In this preferred embodiment, an arsine concentration of approximately one part per billion produces a voltage of approximately 100 milli-volts.

It has been found that by using the single gold film for active layer 13 a phosphine concentration as low as ten parts per billion and an arsine concentration as low as fifteen to twenty parts per billion can be detected. However, by using the gold-palladium alloy film a phosphine concentration that is less than one part per billion and an arsine concentration that is much less than one part per billion can be detected. This characteristic of the gold-palladium film is unexpected because a palladium film alone can only sense phosphine or arsine in concentrations greater than approximately twenty parts per billion. Therefore, it is expected that combining gold and palladium together would result in a sensitivity between those of the individual constituents, that is, detecting concentrations greater than ten and less than twenty parts per billion. The extreme sensitivity of the gold-palladium alloy film is an unexpected result.

By now it should be appreciated that there has been provided a novel sensing element for a gas detector. Utilizing a gold-palladium alloy as the active layer results in detecting extremely low level concentrations of either phosphine or arsine. The less than one part per billion sensing capability is at least an order of magnitude greater than prior sensors. Using a gold film as the active layer permits sensing lower levels of arsine than were achieved with prior arsine sensing elements.

We claim:
1. A gas vapor sensor element comprising:
a substrate having a surface;
a gold-palladium alloy layer on the surface, the alloy layer having an as applied by volume palladium concentration of approximately 1 percent to 20 percent.
2. The gas vapor sensor element of claim 1 wherein the surface is formed of a material selected from the group consisting of silicon, silicon dioxide, silicon nitride, glass, aluminum nitride, aluminum oxide, and mica.
3. The gas vapor sensor element of claim 1 wherein the alloy layer has a thickness of approximately 50 nanometers to 70 nanometers.
4. A method of sensing arsine gas comprising:
exposing a gold film disposed on a substrate to the arsine gas; and
detecting a change in a work function of the gold film.
5. The method of claim 4 wherein exposing the gold film to the arsine gas includes having a concentration of approximately 1 part per billion to 10 parts per billion of the arsine gas.
6. A method of sensing a gas vapor comprising:
exposing a gold-palladium alloy film disposed on a substrate to the gas vapor; and
detecting a change in a work function of the gold-palladium alloy film.
7. The method of claim 6 wherein exposing the gold-palladium alloy film to the gas vapor includes exposing the gold-palladium alloy film to one of arsine or phosphine.
8. The method of claim 7 wherein exposing the gold-palladium alloy film to one of arsine or phosphine includes using the one of arsine or phosphine having a concentration of approximately 1 part per billion to 10 parts per billion.
9. The method of claim 6 wherein exposing the gold-palladium alloy film includes having an as applied by volume palladium concentration of approximately 1 to 20 percent.

* * * * *